United States Patent [19]

Go et al.

[11] Patent Number: 4,808,587
[45] Date of Patent: Feb. 28, 1989

[54] 5-SUBSTITUTED PYRIDO[2,3-D]PYRIMIDINE-2,4-DIONES

[75] Inventors: Kouichiro Go; Yoshiyuki Kurimoto; Norihiko Kitamura, all of Hyogo, Japan

[73] Assignee: Nippon Zoki Pharmaceutical Co., Ltd., Osaka, Japan

[21] Appl. No.: 35,798

[22] Filed: Apr. 8, 1987

[30] Foreign Application Priority Data

Apr. 16, 1986 [JP] Japan .................... 61-89064

[51] Int. Cl.$^4$ ................ C07D 471/04; A61K 31/505
[52] U.S. Cl. .................... 514/258; 544/279; 544/311
[58] Field of Search ................ 514/258; 544/279

[56] References Cited

U.S. PATENT DOCUMENTS 3,272,816  9/1966  Papesch ............... 544/279

FOREIGN PATENT DOCUMENTS 989048  4/1965  United Kingdom ............ 544/279

OTHER PUBLICATIONS

McLean et al., J. Chem. Soc., p. 2582 (1949).
Tominaga et al., Chemical Abstracts, vol. 100, No. 209737y (1984).
Rodgers et al., Chemical Abstracts, vol. 106, No. 156415g (1987).
Matyus et al., Chemical Abstracts, vol. 102, No. 6405g (1985).

Primary Examiner—Donald G. Daus
Assistant Examiner—E. Bernhardt
Attorney, Agent, or Firm—Armstrong, Nikaido, Marmelstein & Kubovcik

[57] ABSTRACT

The present invention relates to a novel pyrido[2,3-d]pyrimidine derivative having the formula (I):

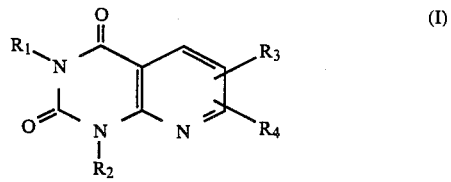

wherein each of $R_1$ and $R_2$, which may be the same or different, is a lower alkyl group; and each of $R_3$ and $R_4$, which may be the same or different, is hydrogen, halogen, hydroxy, nitro, amino, hydroxyamino, hydrazino, azido, a lower alkenylamino group or a lower alkylamino group which may optionally have hydroxy; and pharmaceutically acceptable salt thereof. These compounds are useful as anti-allergic agents, for example, for the treatment of bronchial asthma, urticaria, allergic rhinitis, allergic dermatoses or allergic conjunctivitis.

15 Claims, No Drawings

5-SUBSTITUTED PYRIDO[2,3-D]PYRIMIDINE-2,4-DIONES

BACKGROUND OF THE INVENTION

The present invention relates to novel pyrido[2,3-d]pyrimidine derivatives, pharmaceutically acceptable salts thereof and pharmaceutical compositions containing them as an active ingredient.

It is known that the so-called "chemical mediator", i.e. histamine, serotonin or SRS-A, plays an important role in the appearance of various allergic symptoms in the human body. A pharmaceutical which antagonizes such biochemical substances and/or inhibits their release would be useful for treating or preventing allergic diseases. There have been several prior attempts to synthesize such compounds.

It has now been found that certain pyrido[2,3-d]pyrimidine derivatives have an excellent anti-allergic effect.

An object of the present invention is to provide novel pyrido[2,3-d]pyrimidine derivatives and pharmaceutically acceptable salts thereof useful for treating or mitigating the effects of allergic diseases as well as possessing low toxicity and fewer side effects. Another object of the invention is to provide pharmaceutical compositions containing at least one of the pyrido[2,3-d]pyrimidine derivatives or pharmaceutically acceptable salts thereof as an active ingredient. A further object of the invention is to provide a method for treating mammals suffering from bronchial asthma, urticaria, allergic rhinitis, allergic dermatoses or allergic conjunctivitis which comprises administering thereto the compounds of the present invention.

DETAILED DESCRIPTION OF THE INVENTION

Pyrido[2,3-d]pyrimidine derivatives of the present invention are represented by the following general formula (I):

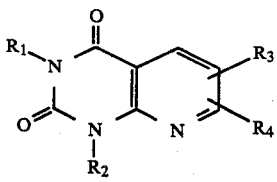

wherein each of $R_1$ and $R_2$, which may be the same or different, is a lower alkyl group; and each of $R_3$ and $R_4$, which may be the same or different, is hydrogen, halogen, hydroxy, nitro, amino, hydroxyamino, hydrazino, azido, a lower alkenylamino group or a lower alkylamino group which may optionally have hydroxy;

Each of $R_1$ and $R_2$, which may be the same or different, represents a straight or branched alkyl group having 1 to 5 carbon atoms, such as methyl, ethyl, propyl, isopropyl, butyl, isobutyl, sec-butyl, tert-butyl or pentyl.

Each of $R_3$ and $R_4$, which may be the same or different, represents hydrogen; halogen, such as fluoride, chloride, bromide or iodide, preferably chloride; hydroxy; nitro; amino; hydroxyamino; hydrazino; azido; a straight or branched alkenylamino group having 2 to 5 carbon atoms, such as vinylamino, propenylamino, isopropenylamino, allylamino, butenylamino or pentenylamino; and a straight or branched alkylamino group having 1 to 5 carbon atoms, such as methylamino, ethylamino, propylamino, isopropylamino, butylamino, isobutylamino, sec-butylamino, tert-butylamino or pentylamino, which may optionally have hydroxy.

Preferred compounds of the present invention include:
1,3-dimethylpyrido[2,3-d]pyrimidine-2,4-dione
5-hydroxy-1,3-dimethylpyrido[2,3-d]pyrimidine-2,4-dione
5-cloro-1,3-dimethylpyrido[2,3-d]pyrimidine-2,4-dione
5-cloro-1,3-diethylpyrido[2,3-d]pyrimidine-2,4-dione
5-cloro-1-isobutyl-3-methylpyrido[2,3-d]pyrimidine-2,4-dione
6-nitro-1,3-dimethylpyrido[2,3-d]pyrimidine-2,4-dione
5-amino-1,3-dimethylpyrido[2,3-d]pyrimidine-2,4-dione
5-amino-1,3-diethylpyrido[2,3-d]pyrimidine-2,4-dione
5-amino-1-isobutyl-3-methylpyrido[2,3-d]pyrimidine-2,4-dione
6-amino-1,3-dimethylpyrido[2,3-d]pyrimidine-2,4-dione
7-amino-1,3-dimethylpyrido[2,3-d]pyrimidine-2,4-dione
7-amino-5-hydroxy-1,3-dimethylpyrido[2,3-d]pyrimidine-2,4-dione
5-methylamino-1,3-dimethylpyrido[2,3-d]pyrimidine-2,4-dione
5-methylamino-1,3-diethylpyrido[2,3-d]pyrimidine-2,4-dione
5-ethylamino-1,3-dimethylpyrido[2,3-d]pyrimidine-2,4-dione
5-isobutylamino-1,3-dimethylpyrido[2,3-d]pyrimidine2,4-dione
5-tert-butylamino-1,3-dimethylpyrido[2,3-d]pyrimidine2,4-dione
5-allylamino-1,3-dimethylpyrido[2,3-d]pyrimidine-2,4-dione
5-hydroxyamino-1,3-dimethylpyrido[2,3-d]pyrimidine-2,4-dione
5-(2-hydroxyethyl)amino-1,3-dimethylpyrido[2,3d-]pyrimidine-2,4-dione
5-hydrazino-1,3-dimethylpyrido[2,3-d]pyrimidine-2,4-dione
5-azido-1,3-dimethylpyrido[2,3-d]pyrimidine-2,4-dione
5-azido-1,3-diethylpyrido[2,3-d]pyrimidine-2,4-dione
5-azido-1-isobutyl-3-methylpyrido[2,3-d]pyrimidine-2,4-dione The pyrido[2,3-d]pyrimidine derivatives of the present invention include pharmaceutically acceptable salts of the compounds having formula (I) above, for example, salts with alkali metal such as sodium or potassium, with alkaline-earth metal such as calcium or barium, or with other metals such as aluminum, salts as acid addition with an inorganic acid such as hydrochloric acid, sulfuric acid, nitric acid or phosphoric acid, or with an organic acid such as formic acid, acetic acid, citric acid or lactic acid; or salts with an organic base such as ammonia or the like. These salts can be prepared from pyrido[2,3-d]pyrimidine derivatives or other salts of these derivatives by a known method.

When optical isomers exist in the compounds of the invention, the present invention includes any of the dl, d and l-isomers.

By using uracil derivatives having the formula (II):

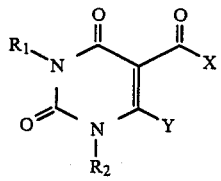

wherein each of $R_1$ and $R_2$ has the same meaning as in the formula (I); X is hydrogen, methyl or cyanomethyl; and Y is amino or dimethylaminomethyleneamino; as a starting material, the compounds of the present invention can be prepared as follows.

(1) when X is methyl and Y is amino in the formula (II), the compounds of the formula (II) and dimethylformamide (DMF) are reacted with a phosphorus oxyhalide such as phosphorus oxychloride, a thionyl halide such as thionyl chloride or a triphenylphosphine dihalide such as triphenylphosphine dichloride or triphenylphosphine dibromide at room temperature or at a suitable temperature above room temperature for several hours to give the compounds of the present invention having halogen such as fluorine, chlorine, bromine or iodine at 5-position.

Further, the said compounds having halogen at 5-position are reacted with ammonia, hydroxyamine, hydrazine, sodium azide, a straight or branched alkenylamino group having 2 to 5 carbon atoms, such as vinylamine, propenylamine, isopropenylamine, allylamine, butenylamine or pentenylamine, or a straight or branched alkylamino group having 1 to 5 carbon atoms such as methylamine, ethylamine, propylamine, isopropylamine, butylamine, isobutylamine, sec-butylamine, tert-butylamine or pentylamine, which may optionally have hydroxy, to introduce a substituent which is amino, a straight or branched alkylamino group having 1 to 5 carbon atoms such as methylamino, ethylamino, propylamino, isopropylamino, butylamino, isobutylamino, sec-butylamino, tert-butylamino or pentylamino, a straight or branched alkenylamino group having 2 to 5 carbon atoms, such as vinylamino, propenylamino, isopropenylamino, allylamino, butenylamino or pentenylamino, hydroxyamino, hydrazino or azido, in substitution for halogen at 5-position.

The above reaction is carried out in an appropriate solvent, e.g. an alcohol such as methanol or ethanol, or DMF, at room temperature, at a suitable temperature above room temperature or under reflux, for several hours. When a substance having low boiling point such as ammonia is used, a sealed tube can be employed.

The compounds of the present invention having halogen or azido at 5-position prepared as mentioned above can be reduced to give the compound of the invention having hydrogen or amino at 5-position by a known method such as catalytic reduction using palladium-carbon (Pd-C).

The compounds of the formula (II), wherein X is methyl and Y is amino, is reacted with dimethylformamide dimethylacetal, dimethylformamide diethylacetal, dimethylformamide dibutylacetal and the like in an appropriate solvent such as DMF at room temperature or at a suitable temperature above room temperature for several hours to give the compounds of the present invention having hydroxy group at 5-position.

The said compounds having halogen at 5-position can be prepared by reacting the compound having hydroxy group at 5-position with a halogenating agent such as oxyphosphorus halide, thionyl halide or triphenylphosphine dihalide as mentioned above.

(2) When X is hydrogen and Y is amino in the formula (I), the compounds of the formula (II) are reacted with cyanomethylenetriphenylphosphorane to give the compounds of the present invention having amino at 7-position. The said preparation according to the Wittig reaction can be carried out by heating under reflux in dried acetonitrile for several hours in a stream of inert gas such as argon.

(3) The compounds of the formula (II), wherein X is hydrogen and Y is dimethylaminomethyleneamino, is reacted with nitromethane in the presence of a base such as triethylamine at room temperature or at a suitable temperature above room temperature for several hours to give the compounds of the present invention having nitro at 6-position.

Further, the resulting compounds are reduced to give the compounds of the invention having amino at 6-position by a known method such as catalytic reduction using Pd-C.

(4) When X is cyanomethyl and Y is amino in the formula (II), the compounds of the formula (I) are reacted with a base such as sodium carbonate at room temperature, at a suitable temperature above room temperature or under reflux for several hours to give the compound having both hydroxy at 5-position and amino at 7-position.

The resulting compounds of the present invention can be purified by known methods such as distillation chromatography and recrystallization. Identification is established through, inter alia, elemental analysis, melting point, IR, NMR, UV, mass spectrum, etc.

EXAMPLES

The following examples, which are illustrative only and not intended to limit the scope of the invention, described the preparation of the compounds of the present invention.

EXAMPLE 1

(1) 5.92 g of 5-acetyl-6-amino-1,3-dimethyluracil and 7.34 g of phosphorus oxychloride were added to 100 ml of DMF. The solution was heated for 2 hr at 60° C. and the solvent was distilled off under reduced pressure After adding water to the residue, the resulting crude crystals were separated from the solution by filtration and recrystallized from ethyl acetate to give 5.34 g of 5-chloro-1,3-dimethylpyrido[2,3-d]pyrimidine-2,4-dione (Compound 1).

Yield: 79% m.p.: 175°–177 ° C.

| Elementary Analysis: $C_9H_8ClN_3O_2$ | | | |
|---|---|---|---|
| | C % | H % | N % |
| Calculated | 47.91 | 3.57 | 18.62 |
| Found | 48.07 | 3.56 | 18.52 |

NMR(DMSO-$d_6$): δ=3.38(3H,s), 3.55(3H,s), 7.40(1H,d,J=5 Hz), 8.55(1H,d,J=5 Hz)

In the same manner, 5-chloro-1,3-diethylpyrido[2,3-d]pyrimidine-2,4-dione and 5-chloro-1-isobutyl-3-methylpyrido[2,3-d]pyrimidine-2,4-dione were obtained.

(2) 0.34 g of Compound 1 was dissolved in 100 ml of methanol and reduced in the presence of Pd-C. Activated charcoal powder was added, and the solution was heated and filtered. The filtrate was distilled under reduced pressure and ethanol was added thereto. The resulting crude crystals were separated from the solution by the filtration and recrystallized from ethanol to give 0.24 g of 1,3-dimethylpyrido[2,3-d]pyrimidine-2,4-dione (Compound 2).
Yield: 84%
m.p.: 160°–161° C.

| Elementary Analysis: $C_9H_9N_3O_2$ | | | |
|---|---|---|---|
| | C % | H % | N % |
| Calculated | 56.54 | 4.75 | 21.98 |
| Found | 56.53 | 4.78 | 21.98 |

NMR(DMSO-$d_6$): δ=3.30(3H,s), 3.55(3H,s), 7.32(1H,dd,J=5 Hz,7.5 Hz), 8.35(1H,dd,J=2.5 Hz,7.5 Hz), 8.68(1H,dd,J=2.5 Hz,5 Hz)

EXAMPLE 2

(1) 1.35 g of Compound 1 was dissolved in 10 ml of DMF and 0.52 g of 90% sodium azide was added thereto. The solution was stirred for 6 hr at room temperature and the solvent was distilled off under reduced pressure. After adding water, the resulting crystals were separated by filtration to give 1.16 g of 5-azido-1,3-dimethylpyrido[2,3-d]pyrimidine-2,4-dione (Compound 3)
Yield: 83%
m.p.: 102°–108° C. (decomposition)
IR(KBr): Vmax=2110 ($N_3$)

In the same manner, 5-azido-1,3-diethylpyrido[2,3-d]pyrimidine-2,4-dione and 5-azido-1-isobutyl-3methylpyrido[2,3-d]pyrimidine-2,4-dione were obtained.

(2) 1.33 g of Compound 3 was dissolved in 400 ml of methanol and reduced in the presence of 300 mg of Pd-C. Activated charcoal powder was added, and the solution was heated and filtered. The filtrate was distilled under reduced pressure and ethanol added thereto. The resulting crude crystals were separated by filtration and recrystallized from ethanol to give 0.87 g of 5-amino-1,3-dimethylpyrido[2,3-d]pyrimidine-2,4-dione (Compound 4).
Yield: 74%
m.p.: 233°–235° C.

| Elementary Analysis: $C_9H_{10}N_4O_2$ | | | |
|---|---|---|---|
| | C % | H % | N % |
| Calculated | 52.42 | 4.89 | 27.17 |
| Found | 52.66 | 4.87 | 26.89 |

NMR(DMSO-$d_6$): δ=3.20(3H,s), 3.40(3H,s), 6.40(1H,d,J=6 Hz), 7.90(1H,d,J=6 Hz), 7.90(2H,br)

In the same manner, the following compounds were obtained.
5-amino-1,3-diethylpyrido[2,3-d]pyrimidine-2,4-dione (Compound 5)
Yield: 64.8%
m.p 216°–217° C.

| Elementary Analysis: $C_{11}H_{14}N_4O_2$ | | | |
|---|---|---|---|
| | C % | H % | N % |
| Calculated | 56.40 | 6.02 | 23.92 |
| Found | 56.54 | 5.99 | 23.86 |

NMR(CDCl$_3$): δ=1.29(3H,t,J=6 Hz), 1.30(3H,t,J=6 Hz), 4.12(2H,q,J=7 Hz), 4.38(2H,q,J=7 Hz), 6.31(1H,d,J=6 Hz), 7.90(1H,br), 8.08(1H,d,J=6 Hz)

5-amino-3-isobutyl-1-methylpyrido[2,3-d]pyrimidine-2,4-dione (Compound 6)
Yield: 67%
m.p.: 183–185° C.

| Elementary Analysis: $C_{12}H_{16}N_4O_2 \cdot 4/25 H_2O$ | | | |
|---|---|---|---|
| | C % | H % | N % |
| Calculated | 57.39 | 6.55 | 22.31 |
| Found | 57.76 | 6.47 | 22.04 |

NMR(DMSO-$d_6$): δ=0.87(6H,d,J=6 Hz), 2.0-2.5(1H,m), 3.29(3H,s), 4.08(2H,d,J=6 Hz), 6.51(1H,d,J=6 Hz), 7.90(1H,br), 8.04(1H,d,J=6 Hz)

EXAMPLE 3

(1) 0.4 g of Compound 1 and 1.86 g of methylamine (30% methanol solution) were added to 10 ml of DMF. The solution was stirred 2 hr at room temperature and the solvent was distilled off under reduced pressure. After adding water, the resulting crude crystals were separated by filtration and recrystallized from ethyl acetate to give 0.23 g of 5-methylamino-1,3-dimethylpyrido[2,3-d]pyrimidine-2,4-dione (Compound 7)
Yield: 63%
m.p.: 179°–180° C.

| Elementary Analysis: $C_{10}H_{12}N_4O_2$ | | | |
|---|---|---|---|
| | C % | H % | N % |
| Calculated | 54.54 | 5.49 | 25.44 |
| Found | 54.40 | 5.48 | 25.21 |

NMR(DMSO-$d_6$): δ=2.85(3H,d,J=5 Hz), 3.19 3.40(3H,s), 6.35(1H,d,J=6 Hz), 8.05(1H,d,J=6 Hz), 8.90(1H,br)

In the same manner, 5-methylamino-1,3-diethylpyrido[2,3-d]pyrimidine-2,4-dione (Compound 8) was obtained.
Yield: 52%
m.p.: 114° C.

| Elementary Analysis: $C_{12}H_{16}N_4O_2 \cdot 2/5 H_2O$ | | | |
|---|---|---|---|
| | C % | H % | N % |
| Calculated | 56.41 | 6.63 | 21.93 |
| Found | 56.15 | 6.42 | 21.90 |

NMR(CDCl$_3$): δ=1.25(3H,t,J=7 Hz), 1.29(3H,t,J=7 Hz), 4.10(2H,q,J=6 Hz), 4.38(2H,q,J=6 Hz), 6.29(1H,d,J=6 Hz), 8.15(1H,d,J=6 Hz), 9.22(1H,br)

(2) Using allylamine or isopropylamine instead of methylamine, the following compounds were obtained.
5-allylamino-1,3-dimethylpyrido[2,3-d]pyrimidine-2,4-dione (Compound 9)
Yield: 72% m.p. 120°–121° C.

| Elementary Analysis: $C_{12}H_{14}N_4O_2$ | | | |
|---|---|---|---|
| | C % | H % | N % |
| Calculated | 58.52 | 5.73 | 22.75 |
| Found | 58.28 | 5.78 | 22.60 |

NMR(CDCl$_3$) δ=3.40(3H,s), 3.64(3H,s), 3.93(2H,m), 4.25(2H,m), 5.80(1H,m), 6.30(1H,d,J=7 Hz), 8.10(1H,d,J=7 Hz), 9.38(1H,br)

5-isopropylamino-1,3-dimethylpyrido[2,3-d]pyrimidine-2,4-dione (compound 10)

Yield: 77.9% m.p.: 127°–128° C.

| Elementary Analysis: $C_{12}H_{16}N_4O_3$ | | | |
|---|---|---|---|
| | C % | H % | N % |
| Calculated | 58.05 | 6.50 | 22.57 |
| Found | 58.13 | 6.68 | 22.58 |

NMR(DMSO-d$_6$): δ=1.23(6H,d,J=6 Hz), 3.23(3H,s), 3.46(3H,s), 3.82(1H,m), 6.49(1H,d,J=6 Hz), 8.05(1H,d,J=6 Hz), 9.07(1H,d,J=8 Hz)

(3) In the same manner, using hydroxylamine hydrochloride instead of methylamine, 5-hydroxyamino-1,3-dimethylpyrido[2,3-d]pyrimidine-2,4-dione (Compound 11) was obtained.

Yield: 84% m.p.: 118°–120° C.

| Elementary Analysis: $C_9H_{10}N_4O_3$ | | | |
|---|---|---|---|
| | C % | H % | N % |
| Calculated | 48.65 | 4.54 | 25.21 |
| Found | 48.85 | 4.45 | 25.34 |

NMR(CDCl$_3$, DMSO-d$_6$): δ=3.39(3H,s), 3.62(3H,s), 6.85(1H,d,J=6 Hz), 8.15(1H,d,J=6 Hz), 9.29(1H,s), 10.55(1H,br)

(4) In the same manner, using hydrazine hydrate instead of methylamine, 5-hydrazino-1,3-dimethylpyrido[2,3d]pyrimidine-2,4-dione (Compound 12) was obtained.

Yield: 90% m.p.: 191°–192° C.

| Elementary Analysis: $C_9H_{11}N_5O_2$ | | | |
|---|---|---|---|
| | C % | H % | N % |
| Calculated | 48.86 | 5.01 | 31.66 |
| Found | 49.12 | 5.05 | 31.60 |

NMR(DMSO-d$_6$): δ=3.24(3H,s), 3.48(3H,s), 4.72(2H,brs), 6.94(1H,d,J=6 Hz), 8.12(1H,d,J=6 Hz), 9.84(1H,brs)

(5) In the same manner, using ethanolamine hydrochloride instead of methylamine, 5-(2-hydroxyethyl-)amino-1,3-dimethylpyrido[2,3-d]pyrimidine-2,4-dione (compound 13) was obtained.

Yield: 68.8% m.p.: 163° C.

NMR(DMSO-d$_6$): δ=3.25(3H,s), 3.48(3H,s), 3.62(2H,ddd,J=6 Hz), 4.95(2H,t,J=5 Hz), 6.48(1H,d,J=6 Hz), 8.05(1H,d,J=6 Hz), 9.26(1H,t,J=5 Hz)

EXAMPLE 4

0.8 g of 5-acetyl-6-amino-1,3-dimethyluracil was dissolved in DMF and 4 ml of dimethylformamide dibutylacetal was added thereto. The solution was heated for 8 hr at 80° C. and distilled under reduced pressure. After purification by silica gel column chromatography, the crude product was recrystallized from ethanol to give 0.59 g of 5-hydroxyl,3-dimethylpyrido[2,3-d]pyrimidine-2,4-dione (Compound 14).

Yield: 70.2% m.p.: 162°–163° C.

| Elementary Analysis: $C_9H_9N_3O_3$ | | | |
|---|---|---|---|
| | C % | H % | N % |
| Calculated | 52.17 | 4.38 | 20.28 |
| Found | 52.31 | 4.29 | 20.32 |

NMR(DMSO-d$_6$): δ=3.30(3H,s), 3.55(3H,s), 6.78(1H,d,J=6 Hz), 8.42(1H,d,J=6 Hz), 12.30(1H,br)

EXAMPLE 5

0.18 g of 6-amino-5-formyl-1,3-dimethyluracil and 0.45 g of cyanomethylenetriphenylphosphorane were added to 20 ml of dried acetonitrile. The solution was heated under reflux for 12 hr in a stream of argon. After cooling, the precipitated crystal was separated by filtration to give 0.08 g of 7-amino-1,3-dimethylpyrido[2,3-d]pyrimidine-2,4-dione (Compound 15).

Yield: 39% m.p.: 290°–295° C.

| Elementary Analysis: $C_9H_{10}N_4O_2$ | | | |
|---|---|---|---|
| | C % | H % | N % |
| Calculated | 52.42 | 4.89 | 27.14 |
| Found | 52.50 | 4.97 | 27.02 |

NMR(CF$_3$COOH): =3.57(3H,s), 3.84(3H,s), 3.84(3H,s), 6.93(1H,d), 8.52(1H,d)

EXAMPLE 6

(1) 0.24 g of 5-formyl-6-dimethylaminomethyleneamino-1,3-dimethyluracil and 0.5 g of triethylamine were added to 10 ml of nitromethane, and the mixture was heated for 2.5 hr at 80° C. After the solvent was distilled off under reduced pressure, ether was added to the residue. The resulting crude crystals were separated by filtration and recrystallized from ether to give 0.14 g of 6-nitro-1,3-dimethylpyrido[2,3-d]pyrimidine-2,4-dione (Compound 16).

Yield: 58.8% m.p.: 203°–205° C.

| Elementary Analysis: $C_9H_8N_4O_4$ | | | |
|---|---|---|---|
| | C % | H % | N % |
| Calculated | 45.76 | 3.41 | 23.72 |
| Found | 45.82 | 3.43 | 23.85 |

NMR(DMSO-d$_6$): δ=3.63(3H,s), 3.81(3H,s), 8.61(1H,d,J=3 Hz), 9.43(1H,d,J=3 Hz)

(2) 0.08 g of Compound 16 was dissolved in methanol and reduced in the presence of 100 mg of Pd-C. Activated charcoal powder was added, and the solution was heated and filtered. The filtrate was distilled under reduced pressure and the residue was recrystallized from methanol to give 0.05 g of 6-amino-1,3-dimethylpyrido[2,3-d]pyrimidine-2,4-dione (Compound 17).
Yield: 71.6%
m.p.: 219°–220° C.
NMR(DMSO-$d_6$)  $\delta=3.30(3H,s)$,  $3.50(3H,s)$, $5.50(2H,s)$, $7.60(1H,d,J=3\ Hz)$, $8.17(1H,d,J=3\ Hz)$

EXAMPLE 7

1.21 g of 6-amino-5-(2-cyanoacetyl)-1,3-dimethyluracil and 2.90 g of sodium carbonate were added to 20 ml of water, and the solution was heated under reflux for 1 hr. After cooling, the precipitate was separated from the solution by filtration to give 1.09 g of 7-amino-5-hydroxy-1,3dimethylpyrido[2,3-d]pyrimidine-2,4-dione (Compound 18).
Yield: 91%
m.p.: >300° C.

| Elementary Analysis: $C_9H_{10}N_4O_3$ | | | |
|---|---|---|---|
| | C % | H % | N % |
| Calculated | 48.65 | 4.54 | 25.22 |
| Found | 48.37 | 4.48 | 25.09 |

NMR(CF3COOH): $\delta=3.52(3H,s)$, $3.81(3H,s)$, $6.20(1H,s)$

EXAMPLE 8

In the same manner as Example 3, the following compounds were obtained:
5-isopropylamino-1,3-dimethylpyrido[2,3-d]pyrimidine-2,4-dione (Compound 19) m.p.: 154° C.
5-(2-hydryxyethyl)amino-1,3-dimethylpyrido[2,3-d]pyrimidine-2,4-dione (Compound 20) m.p.: 152°–154° C.

Pharmaceutical studies on the compounds of the present invention are now described below.

(1) Acute toxicity test

The test compounds were orally administered to groups of 5 ICR-strain male mice. $LD_{50}$ value of the compound of the present invention was calculated by the LitchfieldWilcoxon's method based on mortality for 14 days after drug administration. An example of the results is shown in Table 1.

TABLE 1

| Test compound | $LD_{50}$ (mg/kg) |
|---|---|
| Compound 4 | 850 |
| Compound 5 | >1,000 |
| Compound 7 | 1,050 |
| Compound 9 | >1,000 |
| Compound 10 | 850 |
| Compound 11 | >1,000 |
| Compound 15 | >1,200 |
| Theophylline | 417 |

(2) Anti-allergic effect

PCA (Passive Cutaneous Anaphylaxis) reaction in rats was taken as an index to an anti-allergic effect of the compound of the present invention.

In order to perform sensitization, anti-DNP-Asc (dinitrophenylated Ascaris extracts) serum diluted with saline was injected intradermally at 4 sites on the shaved back of groups of 6 Wister-strain male rats (6 weeks of age). 1 hour after oral administration of the test drug, the mixture of equivalent amount of DNP-Asc (5 mg/ml) and 2% Evans blue were intravenously injected to generate PCA reaction. 30 minutes thereafter, rats were killed by decapitation and exsanguinated. The skin was opened in order to evaluate the leakage of blue dye. The obtained skin was dissolved in 2N potassium hydroxide, then 2N phosphoric acid and acetone were added thereto. The amount of dye was determined by measurement of absorbance at 620 nm after centrifugation. An example of the results is shown in Table 2.

TABLE 2

| Test compound | Dosage (mg/kg) | Inhibition (%) |
|---|---|---|
| control | — | 0 |
| Compound 2 | 20 | 51.2 |
| Compound 4 | 20 | 68.7 |
| Compound 5 | 20 | 79.2 |
| Compound 7 | 20 | 73.7 |
| Compound 8 | 20 | 76.4 |
| Compound 9 | 20 | 67.9 |
| Compound 10 | 20 | 86.6 |
| Compound 11 | 20 | 74.0 |
| Compound 14 | 20 | 49.9 |
| Compound 15 | 20 | 68.7 |
| Compound 17 | 20 | 56.2 |
| Theophylline | 20 | 57.9 |

As a clearly apparent from the above mentioned results, the pyrido[2,3-d]pyrimidine derivatives of the present invention have excellent anti-allergic properties which are superior to those of conventional pharmaceuticals, for example, theophilline. Furthermore, the compounds of the invention possess low toxicity, so that they have good safety properties. They are useful in the prevention or treatment of various allergic diseases, such as bronchial asthma, urticaria, allergic rhinitis, allergic dermatoses or allergic conjunctivitis. In addition, since the compounds of the present invention can be administered orally, they can be used in the treatment of chronic diseases.

As another index of anti-allergic effect of the compound of the present invention different from the PCA reaction, the phosphodiesterase (PDE) inhibiting effect was tested. As the results, the compounds of the present invention effectively inhibited PDE activity even at very low concentrations. The compounds of the present invention have excellent PDE inhibiting effect, so that they are not only useful as anti-allergic agents, but also as cardiotonics, bronchdilator and the like.

The compounds of the present invention can be made into pharmaceutical compositions by combination with appropriate medicial carriers or diluents, and can be formulated into preparations in solid, semisolid, liquid or gaseous form such as tablets, capsules, powders, granules, ointments, solutions, suppositories, injections, inhalants, aerosols and cataplasms in usual ways for oral or parenteral administrations.

In pharmaceutical dosage forms, the compounds of the present invention can be used in the form of their pharmaceutically acceptable salts, and also can be used alone or in appropriate association, as well as in combination with other pharmaceutically active components such as a bronchodilator, artihistaminic or tranquilizer.

In case of oral preparations, the compounds can be used alone or combined with appropriate additives to make tablets, powders, granules or capsules, e.g. with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethylcellulose; with lubricants such as talc or magnesium stearate; and if desired, with diluents, buffering agents, moistening agents, preservatives and flavoring agents.

The compounds of the invention can also be made into an ointment by conbination with an ointment base such as vaseline, paraffin, plastibase, simple ointment, hydrophilic ointment, hydrophilic vaselin or hydrophilic plastibase.

Furthermore, the compounds of the invention can be made into a suppository by mixing with a variety of bases, e.g. fatty and oily base such as cacao butter, emulsifying base or water-soluble base such as macrogol.

The compounds of the present invention can be formulated into a preparations for injections by dissolving, suspending or emulsifying in aqueous or non-aqueous solvent, such as distilled water for injection, physiologically saline solution, vegetable oil, synthetic aliphatic acid glycerides, esters of higher aliphatic acid or propylene glycol.

In case of inhalations or aerosol preparations, the compounds of the invention in the form of a liquid or minute powder can be filled up in an aerosol container with gas or liquid spraying agent, and if desired, with conventional adjuvants such as humidifying agents or dispersing agent. They can also be used as pharmaceuticals for a non-pressurized preparation such as in a nebulizer or an atomizer.

In order to make the compounds of the present invention into collyriums, they can be prepared as a solution or suspension together with an aqueous solvent such as sterile, purified water and physiologically saline solution, or a non-aqueous solvent for injection.

Cataplasms can be prepared by mixing the compounds with mentha oil, concentrated glycerin, kaolin or other suitable additives.

The desirable dose of the compounds of the present invention varies with the subject, form of the drug, method and period of administration. However, in order to obtain desirable effects, generally it is recommended to administer orally 1 to 1000 mg, preferably 5 to 600 mg daily. Unit preparations are also recommended for administration in one to several units daily.

In case of parenteral administrations e.g. injections, doses of the compounds in the order of one tenth to one third of the above dose are preferable as daily doses.

Some prescriptions of the pharmaceutical compositions are shown below as examples which contain the compounds of the present invention as active ingredients.

| Prescription example 1 (tablet) | |
|---|---|
| Component | Content in a tablet (mg) |
| compound of this invention | 100 |
| lactose | 130 |
| corn starch | 40 |
| magnesium stearate | 10 |
| Total | 280 mg |

| Prescription example 2 (capsule) | |
|---|---|
| Component | Content in a capsule (mg) |
| compound of this invention | 50 |
| lactose | 250 |
| Total | 300 mg |

| Prescription example 3 (injection) | |
|---|---|
| Component | Content in an ampule (mg) |
| compound of this invention | 10 |
| sodium chloride | proper amount |
| distilled water for injection | proper amount |
| Total | 1 ml |

| Prescription example 4 (ointment) | |
|---|---|
| Component | Weight (g) |
| compound of this invention | 1 |
| emulsified wax | 30 |
| white petrolatum | 50 |
| liquid paraffin | 20 |
| Total | 101 g |

| Prescription example 5 (suppository) | |
|---|---|
| Component | Content in a suppository (mg) |
| compound of this invention | 20 |
| cacao butter | 1980 |
| Total | 2000 mg |

| Prescription example 6 (inhalation) | |
|---|---|
| Component | Content in a inhalation (g) |
| compound of this invention | 1 |
| lactose | 5 |
| Total | 6 g |

What is claimed is:

1. A pyrido[2,3-d]pyrimidine compound having the following formula (I):

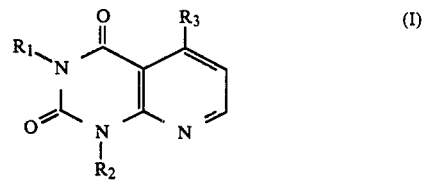

wherein each $R_1$ and $R_2$, which may be the same or different, is a lower alkyl group; and $R_3$ is halogen, hydroxy, nitro, amino, hydroxdyamino, hydrazino, azido, a lower alkenylamino group or a lower alkylamino group which may optionally have hydroxy; or a pharmaceutically acceptable salt thereof with the proviso that when $R_1$ and $R_2$ are methyl, $R_3$ is not amino. salt thereof.

2. A pyrido[2,3-d]pyrimidine compound according to claim 1 wherein $R_3$ is amino, or a pharmaceutically acceptable salt thereof.

3. A pyrido[2,3-d]pryirimidine compound according to claim 2 wherein $R_1$ and $R_2$ are ethyl, or a pharmaceutically acceptable salt thereof.

4. A pyrido[2,3-d]pyrimidine compound according to claim 1 wherein $R_3$ is a lower alkylamino group, or a pharmaceutically acceptable salt thereof.

5. A pyrido[2,3-d]pyrimidine compound according to claim 4 wherein $R_3$ is methylamino, or a pharmaceutically acceptable sale thereof.

6. A pyrido[2,3-d]pyrimidine compound according to claim 4 wherein $R_3$ is ethylamino, or a pharmaceutically acceptable salt thereof.

7. A pyrido[2,3-d]pyrimidine compound according to claim 4 wherein $R_3$ is propylamino, or a pharmaceutically acceptable salt thereof.

8. A pyrido[2,3-d]pyrimidine compound according to claim 4 wherein $R_3$ is isopropylamino, or a pharmaceutically acceptable salt thereof.

9. A pyrido[2,3-d]pyrimidine compound according to claim 4 wherein $R_1$ and $R_2$ are methyl, or a pharmaceutically acceptable salt thereof.

10. A pyrido pryimidine compound according to claim 4 wherein $R_1$ and $R_2$ are ethyl, or a pharmaceutically acceptable salt thereof.

11. A pyrido[2,3-d]pyrimidine compound according to claim 1, wherein $R_3$ is hydroxyamino, or a pharmaceutically acceptable salt thereof.

12. An anti-allergic composition which comprises a pharmaceutically acceptable carrier and an effective amount of a pyrido[2,3-d]pyrimidine compound having the formula (I):

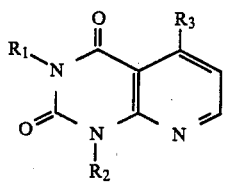

(I)

wherein each of $R_1$ and $R_2$, which may be the same or different, is a lower alkyl group and $R_3$ is halogen, hydroxy, nitro, amino, hydroxyamino, hydrazino, azido, a lower alkenylamino group or a lower alkylamino group which may optionally have hydroxy; or a pharmaceutically acceptable salt thereof with the proviso that when $R_1$ and $R_2$ are methyl $R_3$ is not amino.

13. An anti-allergic composition according to claim 12 wherein $R_3$ is amino, or a pharmaceutically acceptable salt thereof.

14. A method for preventing or treating allergic disease in a mammal which comprises administering to the mammal and anti-allergic effective amount of a pyrido[2,3-d]pyrimidine compound having the following formula (I):

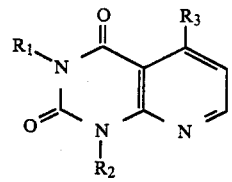

(I)

wherein each $R_1$ and $R_2$, which may be the same or different, is a lower alkyl group; and $R_3$ is halogen, hydroxy, nitro, amino, hydroxyamino, hydrazino, azido, a lower alkenylamino group or a lower alkylamino group which may optionally have hydroxy; or a pharmaceutically acceptable salt thereof.

15. A method according to claim 14 wherein $R_3$ is amino, or a pharmaceutically acceptable salt thereof.

* * * * *